United States Patent
Viehweg et al.

(10) Patent No.: US 8,979,783 B2
(45) Date of Patent: Mar. 17, 2015

(54) ORTHOPEDIC DEVICES, SYSTEMS, AND METHODS OF USE

(76) Inventors: Tate L. Viehweg, Lehi, UT (US);
Michael Wagstaff, Farmington, UT (US)

(*) Notice: Subject to any disclaimer, the term of this patent is extended or adjusted under 35 U.S.C. 154(b) by 254 days.

(21) Appl. No.: 13/366,145

(22) Filed: Feb. 3, 2012

(65) Prior Publication Data
US 2013/0204172 A1 Aug. 8, 2013

(51) Int. Cl.
- A61F 5/00 (2006.01)
- A61F 5/01 (2006.01)
- A61F 13/06 (2006.01)
- A61F 13/10 (2006.01)
- A61L 15/12 (2006.01)

(52) U.S. Cl.
CPC ............ *A61F 13/062* (2013.01); *A61F 5/0102* (2013.01); *A61F 5/0109* (2013.01); *A61F 5/0111* (2013.01); *A61F 5/0118* (2013.01); *A61F 5/0125* (2013.01); *A61F 5/013* (2013.01); *A61F 13/066* (2013.01); *A61F 13/105* (2013.01); *A61L 15/12* (2013.01)
USPC .............................................. 602/23; 602/27

(58) Field of Classification Search
USPC ............ 602/3, 5, 7–8, 41, 44–45, 50, 60–62; 2/61, 239, 242
See application file for complete search history.

(56) References Cited

U.S. PATENT DOCUMENTS

| | | | |
|---|---|---|---|
| 3,329,143 A * | 7/1967 | Gordon | 602/3 |
| 4,136,686 A | 1/1979 | Arluck | |
| 4,372,298 A | 2/1983 | Lerman | |
| 5,439,438 A * | 8/1995 | Ersfeld et al. | 602/3 |
| 5,501,659 A | 3/1996 | Morris et al. | |
| 5,899,872 A * | 5/1999 | Gilmour | 602/65 |
| 6,047,403 A * | 4/2000 | Juozaitis | 2/61 |
| 6,117,098 A | 9/2000 | Weber et al. | |
| 6,652,474 B1 | 11/2003 | Quinn et al. | |
| 6,767,332 B1 | 7/2004 | Pardue et al. | |
| 6,875,190 B2 | 4/2005 | Reinhardt | |
| 7,128,725 B2 | 10/2006 | Rabe | |
| 7,166,760 B1 | 1/2007 | Talbot | |
| 7,896,828 B1 | 3/2011 | Shirley | |
| 7,931,567 B2 | 4/2011 | Rosenberg et al. | |
| 7,992,243 B2 | 8/2011 | Cook et al. | |
| 8,048,012 B1 | 11/2011 | Castro | |
| 2004/0199092 A1* | 10/2004 | Biewend et al. | 602/3 |
| 2008/0195009 A1* | 8/2008 | Satkowiak | 602/3 |
| 2009/0024065 A1* | 1/2009 | Einarsson | 602/26 |
| 2011/0270435 A1 | 11/2011 | Hyde et al. | |

OTHER PUBLICATIONS

ALPHAWIRE, Fit Heat-Shrink Tubing, Brochure, 2009.

* cited by examiner

*Primary Examiner* — Michael A. Brown
(74) *Attorney, Agent, or Firm* — Workman Nydegger

(57) ABSTRACT

Orthopedic devices, systems, and methods of using the same are disclosed. In an embodiment, an orthopedic device intended for use with at least one moveable body part of a user may comprise a tubular body forming an interior surface and an exterior surface. The tubular body may include at least one opening and one or more shrinkable materials. The tubular body may be moveable between a first position, wherein the tubular body is configured to at least partially receive and at least partially surround the at least one moveable body part of the user, and a second position, wherein one or more portions of the tubular body are configured to generally conform to and at least partially restrict movement of the at least one moveable body part in one or more directions. The tubular body may be configured to move from the first position to the second position in response to a treatment.

18 Claims, 18 Drawing Sheets

ORTHOPEDIC DEVICES, SYSTEMS, AND METHODS OF USE

BACKGROUND

Orthopedic devices is a broad term that is used to describe medical structures such as casts, splints, supports, braces, and other means utilized to support, immobilize, restrain, protect and position body portions. Orthopedic devices are used in many fields, including the physical medicine and rehabilitation field, general medicine, neurological field. Orthopedic devices are also used to prevent recurrence of previous disabilities, and to prevent discomfort and subsequent disability.

Different types of known orthopedic devices have specific uses. As one example, plaster casts are commonly used for the treatment of fractures. However, plaster casts can take hours to harden, are excessively heavy, commonly have poor compression strength, are readily crushed or broken, and characteristically have poor resistance to water. As another example, ankle injuries are commonly treated with ankle supports in the form of ankle wraps and/or athletic tape. However, wrapping and/or taping ankles is notoriously a slow cumbersome process, expensive, inherently inconsistent, and requires the talent of a well skilled person. These are only a few of many examples demonstrating the need for orthopedic devices that are practical, suitable for their intended purpose, and capable of being formed in a customizable, generally consistent, convenient, effective, and timely manner.

SUMMARY

Orthopedic devices, systems, and methods of using the same are disclosed. In an embodiment, an orthopedic device intended for use with at least one moveable body part of a user may comprise a tubular body forming an interior surface and an exterior surface. The tubular body may include at least one opening and one or more shrinkable materials. The tubular body may be moveable between a first position, wherein the tubular body is configured to at least partially receive and at least partially surround the at least one moveable body part of the user, and a second position, wherein one or more portions of the tubular body are configured to generally conform to and at least partially restrict movement of the at least one moveable body part in one or more directions. The tubular body may be configured to move from the first position to the second position in response to a treatment. In an embodiment, the treatment may comprise a heat treatment, a chemical treatment, and/or an ultraviolet light treatment.

In another embodiment, an orthopedic system intended for use with at least one moveable body part of a user may comprise a tubular body forming an interior surface and an exterior surface. The tubular body may include at least one opening and one or more shrinkable materials. The tubular body may be moveable between a first position, wherein the tubular body is configured to at least partially receive and surround the at least one moveable body part of the user, and a second position, wherein the tubular body is configured to generally conform to and at least partially support the at least one moveable body part. The tubular body may be configured to move from the first position to the second position in response to a treatment. The orthopedic system may further include a liner and an intermediate layer interposed between the line and the interior surface of the tubular body. The intermediate layer may be configured to substantially protect the at least one moveable body part of the user from the treatment.

In yet another embodiment, a method for bracing a moveable body part of a user may comprise receiving a tubular body. The tubular body may include at least one opening and one or more shrinkable materials. The tubular body may be moveable between a first position, wherein the tubular body is configured to generally receive and generally surround the moveable body part of the user, and a second position, wherein the tubular body is configured to substantially conform to and at least partially restrict movement of the at least one moveable body part in one or more directions. The method may further include positioning the moveable body part substantially within the tubular body with the tubular body in the first position. The method may also include applying a treatment to the tubular body to move the tubular body from the first position to the second position.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

To further clarify at least some of the advantages and features of the present disclosure, a more particular description of the disclosure will be rendered by reference to specific embodiments thereof which are illustrated in the appended drawings. It is appreciated that these drawings depict only illustrated embodiments of the disclosure and are therefore not to be considered limiting of its scope. The disclosure will be described and explained with additional specificity and detail through the use of the accompanying drawings in which:

FIG. 1B illustrates a back elevation view of the ankle support shown in FIG. 1A;

FIG. 1C illustrates a cross-sectional view of the ankle support shown in FIG. 1B taken along line 1C-1C;

Figure 1A:
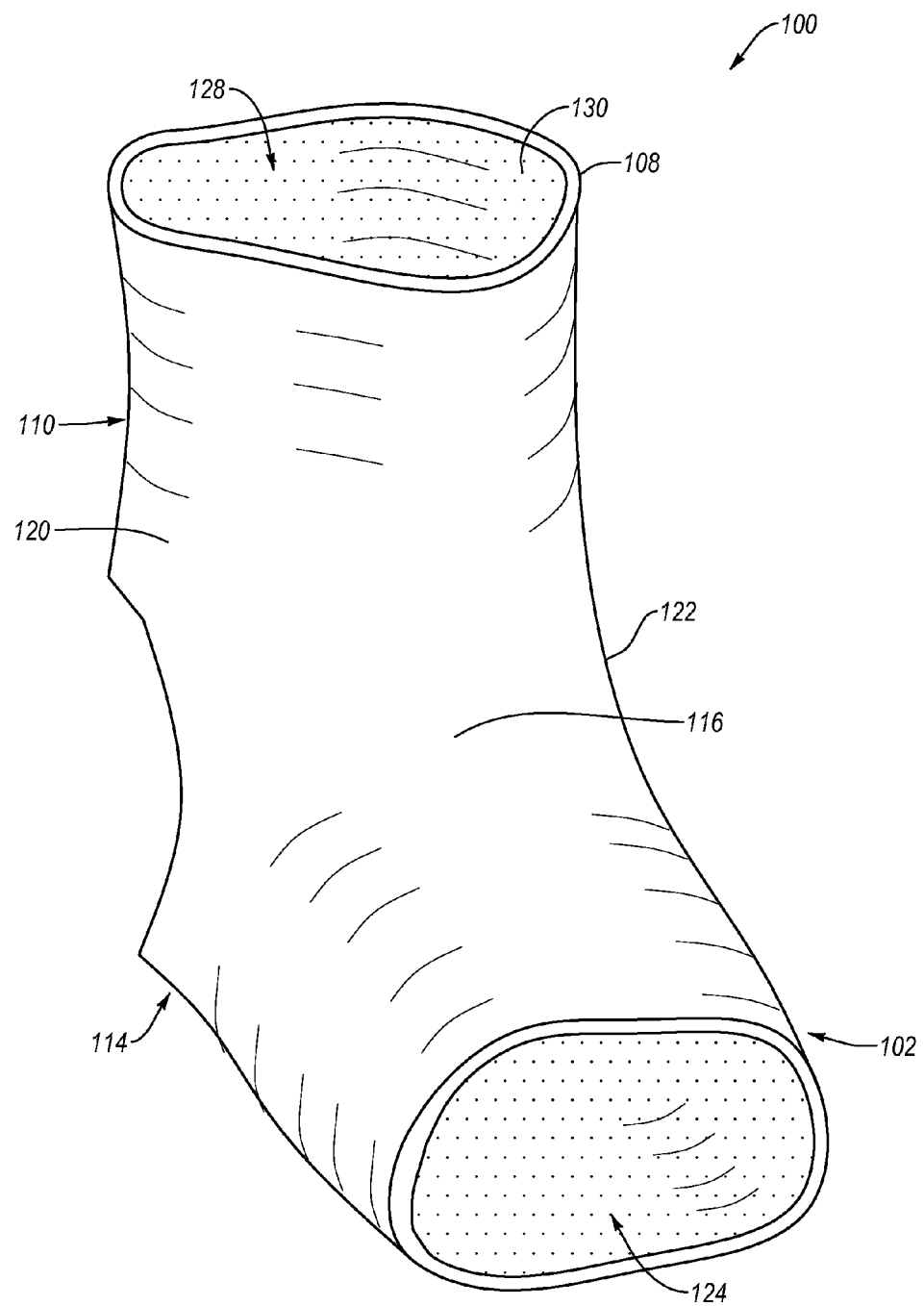
FIG. 1A illustrates a perspective view of an ankle support according to an embodiment.

It should be noted that the figures are not drawn to scale and that elements of similar structures or functions are generally represented by like reference numerals for illustrative purposes throughout the figures. It also should be noted that the figures are only intended to facilitate the description of example configurations of the present disclosure.

DETAILED DESCRIPTION

Embodiments of the invention relate to orthopedic devices and systems that include features configured to conform the orthopedic devices and systems to one or more moveable body parts and to selectively support the same.

FIG. 1A is a perspective view of an orthopedic device comprising an ankle brace 100 according to an embodiment. FIG. 1B is a back elevation view of the ankle brace 100 shown in FIG. 1A. As shown, the ankle brace 100 may include a tubular body 102 forming an interior surface 106 and an exterior surface 108 (shown in FIG. 1D). As shown, the ankle brace 100 may include a liner 130 configured to help secure the ankle brace 100 to the foot, ankle, and/or leg of the user, protect the user, support the foot, ankle, and/or leg, and/or provide a comfortable fit. In an embodiment, the liner 130 may include a plurality of small perforations for enhanced flexibility and/or ventilation of the ankle brace 100. The body 102 may be at least partially defined by a front portion 116, a back portion 118, a first side portion 120, and a second side portion 122 and may include a foot portion 114 and a leg portion 110. The foot portion 114 may be sized and configured to receive and substantially surround a foot and an ankle. As shown, the foot portion 114 may also include a first opening 124 configured to allow toes of the user to extend therethrough and a second opening 126 on the back portion 118 configured to receive a heel of a user. In other embodiments, the first opening 124 and/or the second opening 126 may be omitted. The leg portion 110 may be sized and configured to at least partially surround and/or cover a lower portion of a leg. The leg portion 110 may include a third opening 128 sized and configured to allow the foot and the lower portion of the leg to be positioned within the body 102. In an embodiment, the body 102 may comprise a single member. In other embodiments, the body 102 may comprise two, three, four, or any other suitable numbers of members. For example, the leg portion 110 and the foot portion 114 may be attached to one another via stitching, adhesives, fasteners, combinations thereof, or other suitable attachment means. In addition, the leg portion 110 and the foot portion 114 may be attached to one another via two or more connecting members or stirrups. One will appreciate that the ankle brace 100 may be configured to be used on a user's right ankle or left ankle.

In an embodiment, the ankle brace 100 may include one or more features configured to selectively move the ankle brace 100 between a receiving position, wherein the ankle brace 100 may receive and/or generally surround the leg, the ankle, and/or the foot, and a supporting position, wherein one or more portions of the ankle brace 100 substantially conforms to and/or at least partially restrict movement of the ankle in one or more directions. For example, the body 102 may be made from a variety of different shrinkable materials that are configured to shrink the ankle brace 100 into the receiving position in response to a treatment. Shrinkable materials are materials capable of being reduced in size in response to a treatment. Specifically, the tubular body 102 may comprise one or more thermoplastic materials, polyolefin, polyolefin elastomer, nylon, neoprene, silicone rubber, woven fabric, combinations thereof, or other suitable shrinkable materials. In an embodiment, the shrinkable materials may be uniform throughout the body 102. In other embodiments, the shrinkable materials may vary at different locations on the body 102. For example, the first side portion 120 and the second side portion 122 in the area of the user's ankle may comprise a shrink material that in the supporting position becomes generally stiff or rigid to at least partially restrict abnormal eversion and/or inversion of the ankle. In addition, the front portion 116 in the area of a user's lower leg portion may comprise a shrink material that in the supporting position remains generally flexible to generally allow dorsiflexion and/or plantar flexion.

In an embodiment, the shrinkable materials may be configured to control the amount of shrinkage of the ankle brace 100. For example, one or more of the shrinkable materials may have a shrink ratio between about 7:1 to 1.1:1; 6:1 to 1.3:1; 5:1 to 1.5:1; or 4:1 to 2:1. The shrink ratio is the quantitative relation between the initial size of the body 102 and the shrunken size of the body 102. In another embodiment, the ankle brace 100 may include shrinkable materials having different shrink ratios in different locations on the ankle brace 100. For example, the leg portion 110 may include one or more shrinkable materials having shrink ratios relatively smaller than one or more shrinkable materials in the foot portion 114.

In an embodiment, a treatment 236 (shown in FIG. 2C) may be configured to shrink the ankle brace 100 to move the ankle brace 100 from the receiving position to the supporting position. The treatment 236 may comprise a heat treatment, a chemical treatment, a water treatment, a cold temperature treatment, an electromagnetic radiation treatment such as ultraviolet light, combinations thereof, or other suitable treatments. For example, the treatment 236 may comprise a heat treatment and the ankle brace 100 may have a shrink temperature between about 140 degrees Fahrenheit (° F.) to 500° F.; about 175° F. to 450° F.; about 200° F. to 400° F.; or about 250° F. to 350° F. The shrink temperature is the minimum temperature at which a shrinkable material shrinks. The shrink temperature may be configured to reduce the risk of injuring the user. For example, the shrink temperature may be between about 140° F. and 200° F. In other embodiments, the shrink temperature may be configured to reduce the risk of accidental shrinkage of the ankle brace 100. For example, the shrink temperature may be between about 225° F. and 400° F.

In other embodiments, the treatment 236 may comprise a chemical treatment. For example, after the ankle brace 100 is placed on the user, the ankle brace 100 and at least the foot and/or ankle of the user may be submersed in a chemical solution or the ankle brace 100 may be treated with a spray-on chemical treatment configured to shrink the ankle brace 100. In other embodiments, the treatment may comprise an electromagnetic radiation treatment. For example, the treatment 236 may comprise ultraviolet light treatment, an infrared light treatment, or other suitable electromagnetic radiation treatments configured to shrink the ankle brace 100.

In yet other embodiments, the treatment 236 may comprise one or more treatments. For example, the treatment 236 may comprise a first heat treatment to shrink the angle brace into the supporting position and a second chemical treatment to stiffen and/or relax at least part of the ankle brace 100.

Such a configuration of the ankle brace 100 may allow the ankle brace 100 to be customizable and/or conformable to a user in a minimal amount of time in a variety of applications.

Figure 1D:
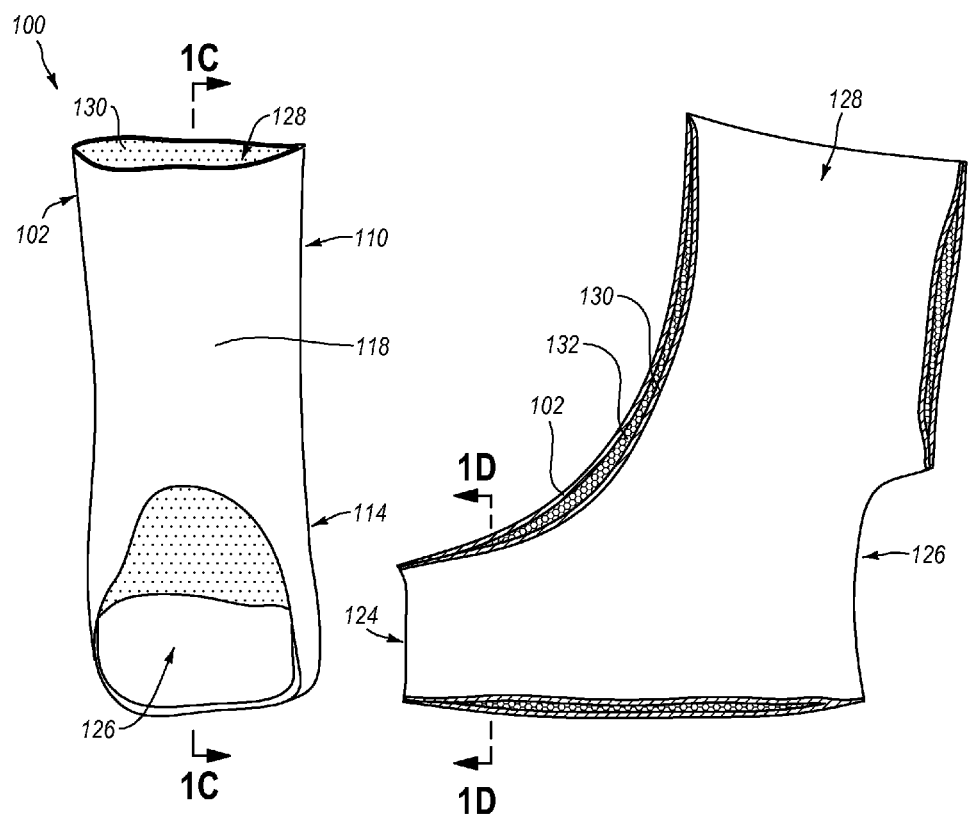
FIG. 1D illustrates a cross-sectional view of the ankle support shown in FIG. 1C taken along line 1D-1D.
Figure 1D:
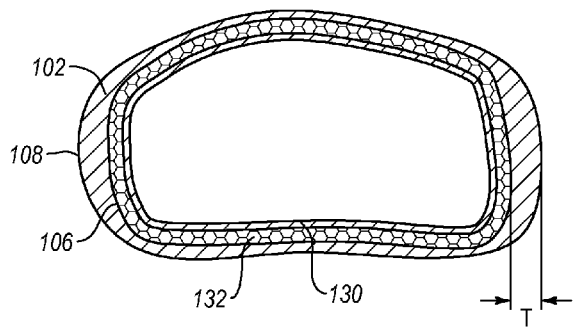

Referring now to FIGS. 1C and 1D, the ankle brace 100 may include the body 102, the liner 130, and an intermediate layer 132. As shown, the body 102 may have a thickness T extending between the interior surface 106 and the exterior surface 108 of the body 102. In an embodiment, the body 102 has a thickness T of about 0.5-millimeters (mm) to 5-mm. In other embodiments, the thickness T may be about 0.5-mm to 30-mm; 2-mm to 20-mm; or 3-mm to 10-mm. The thickness T may be generally thinner to provide a more lightweight construction of the body 102 or the thickness T may be generally thicker to provide a more robust construction of the body 102. In other embodiments, the thickness T may be either greater or smaller. In an embodiment, the thickness T of the body 102 may be generally uniform. In other embodiments, the thickness T of the body 102 may vary based on the anatomy of the user. For example, the body 102 may have a greater thickness T about the ankle and a lesser thickness T about the foot of the user. Such a configuration of the body 102 may provide additional support to the ankle and/or may allow the ankle brace 100 to be more comfortably positioned within a shoe. In addition, the foot portion 114 of the body 102 may include a greater thickness T along at least a portion of the bottom of the foot to provide additional cushioning to the user and/or arch support.

In yet other embodiments, the thickness T of the body 102 may vary to influence stiffness and/or flexibility of the ankle brace 100 in different locations. Controlling the flexibility and/or stiffness of the ankle brace 100 in different locations may allow the ankle brace to maintain its structural integrity while providing desired support, protection, positioning, and/or restraint. For example, as shown in FIG. 1D, the first side portion 120 and the second side portion 122 of the body 102 may have a greater thickness T than at least the front portion 116 of the body 102. Such a configuration may provide additional lateral support to the user and/or may substantially restrict abnormal eversion and/or inversion while allowing dorsiflexion and/or plantar flexion. The thickness T of the body 102 may also be configured to substantially immobilize the ankle. For example, the body 102 may have a greater thickness T about the front, back and sides of the ankle of the user such that the ankle brace 100 provides sufficient stiffness and/or rigidity about the ankle to substantially immobilize the ankle. Accordingly, the ankle brace 100 may be configured for use in a variety of applications including sports, medical treatment, emergency response, or other suitable applications.

In an embodiment, the liner 130 may be attached to the interior surface 106 of the body 102 along at least a portion of one or more edges of the liner 130. In other embodiments, the liner 130 may be separate from the body 102 and/or the ankle brace 100. For example, the liner 130 may be configured as a protective sock and may be placed on the user prior to placement of the body 102 and/or the ankle brace 100 on the user. In yet other embodiments, the liner 130 may be omitted. The liner 130 may be sized and/or configured to provide a comfortable fit for the user as well as stability. For example, the liner 130 may be comprised of a soft, compressible material such as polyurethane foam, polyethylene foam, microspheres contained in a lubricant matrix, other gels and foams, pneumatics, combinations thereof, or other suitable materials. In other embodiments, the liner 130 may comprise a thermoplastic material that once shrunk, remains relatively flexible and comfortable. Similar to the body 102, the liner 130 may have a thickness that is substantially uniform or varies based on anatomy, desired flexibility, and/or a desired stiffness of the liner 130. The liner 130 may also be sized and/or configured to at least partially protect the user from the treatment 236. For example, the treatment 236 may comprise a heat treatment and the liner 130 may be configured as a protective layer to generally insulate the user from the heat treatment. In another embodiment, the treatment may comprise a chemical treatment and the liner 130 may be configured to provide an impermeable barrier to substantially protect the user from the chemical treatment.

The intermediate layer 132 may be interposed between the interior surface 106 of the body 102 and the liner 130. Similar to the liner 130, the intermediate layer 132 may be sized and/or configured to provide a comfortable fit, stability, and/or protection to a user from the treatment 236. For example, the intermediate layer 132 may have a thickness preconfigured to provide a physical barrier between the user and the treatment 236. In another embodiment, the intermediate layer 132 may comprise one or more insulation materials configured to at least partially protect the user from a treatment 236 comprising a heat treatment. For example, the intermediate layer 132 may comprise polyurethane, elastomeric foam, mineral wool, phenolic foam, polystyrene, combinations thereof, of any other suitable insulation materials. In yet other embodiments, the intermediate layer 132 may be configured to dissipate heat before heat from a heat treatment reaches the liner 130 and/or the user. For example, the intermediate layer 132 may comprise water, air, gels, combinations, thereof, or any suitable heat dissipating material. Moreover, similar to the body 102, the thickness of the intermediate layer 132 may be substantially uniform or may vary based on anatomy, desired flexibility, and/or a desired stiffness of the liner 130.

Figure 2A:
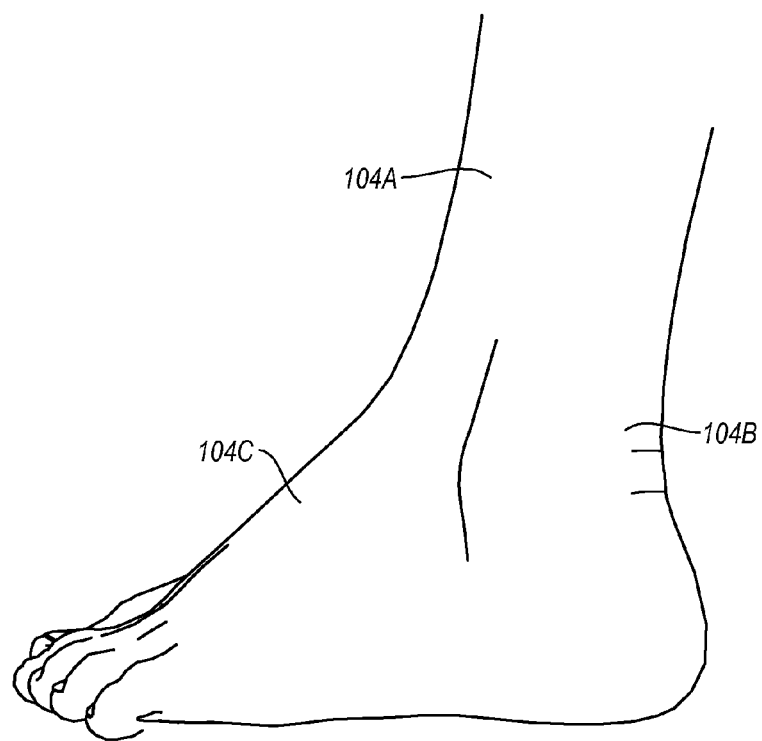
FIGS. 2A-2E illustrate perspective views illustrating exemplary steps in a method of using the ankle support shown in FIG. 1A.
Figure 2A:
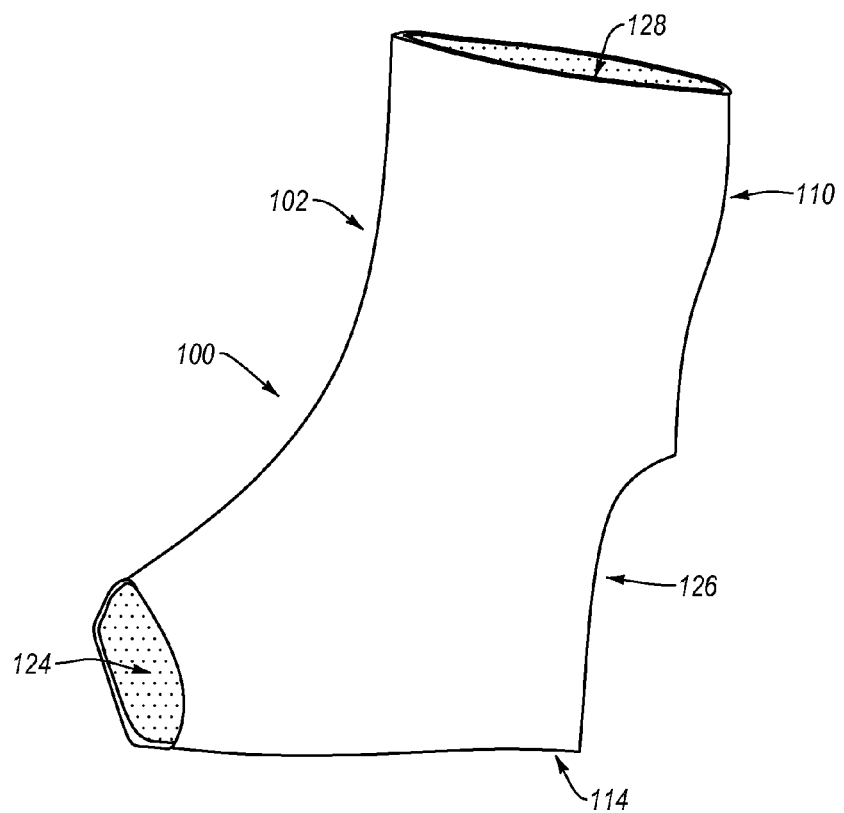
Figure 2B:
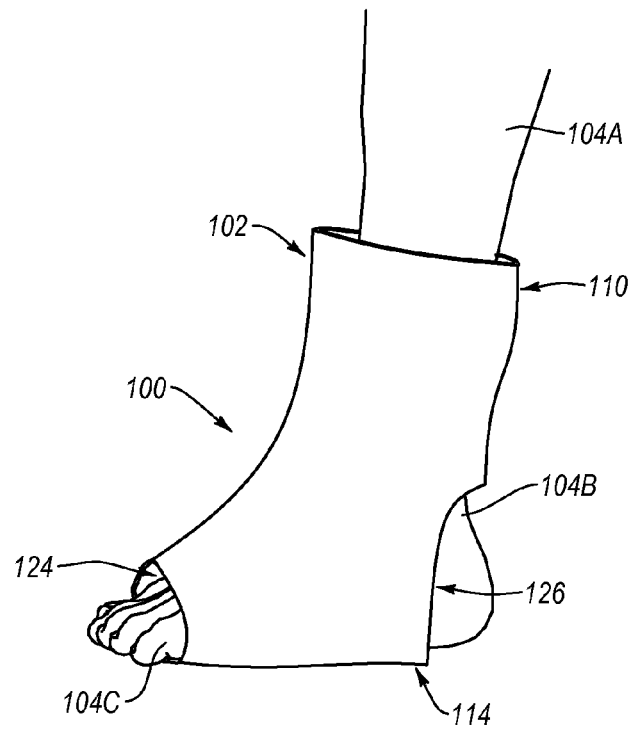

A method of using the ankle brace 100 according to an embodiment will now be described in relation to FIGS. 2A-2E. As shown in FIG. 2A, the method may include the step of positioning the ankle brace 100 proximate the leg 104A, ankle 104B, and foot 104C of the user. With the ankle brace 100 in the receiving position, the foot, ankle, and leg may then be placed into the ankle brace 100 as shown in FIG. 2B. In the receiving position, the foot portion 114 of the body 102 may loosely surround the foot and ankle. The toes of the user may extend past the first opening 124. In other embodiments, the toes may be positioned within the foot portion 114 with the ankle brace 100 in the receiving position. The heel of the foot 104C may be generally positioned within the second opening 126. As shown, the leg portion 110 may cover and loosely surround the front of the lower leg. Such a configuration may allow the ankle brace 100 to be easily and quickly positioned over the ankle 104B and/or foot 104C.

Figure 2C:
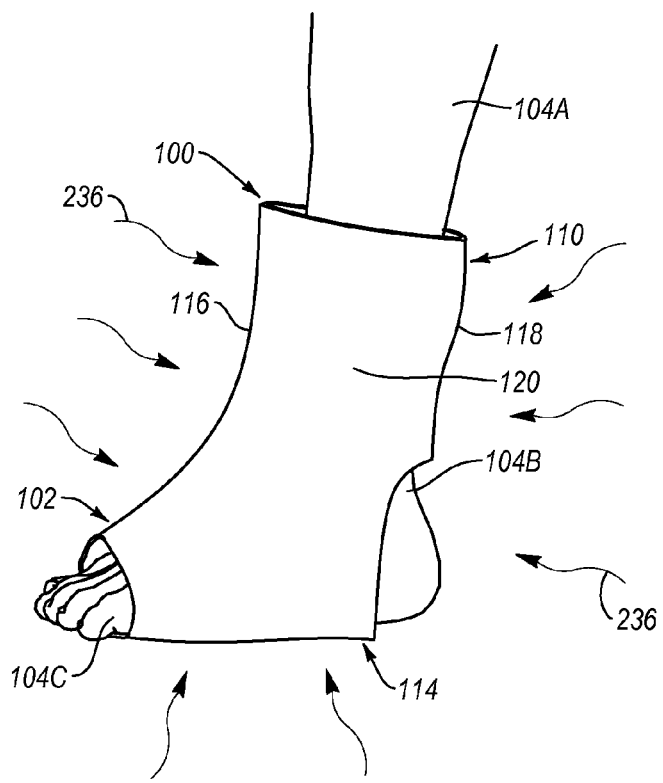
Figure 2D:
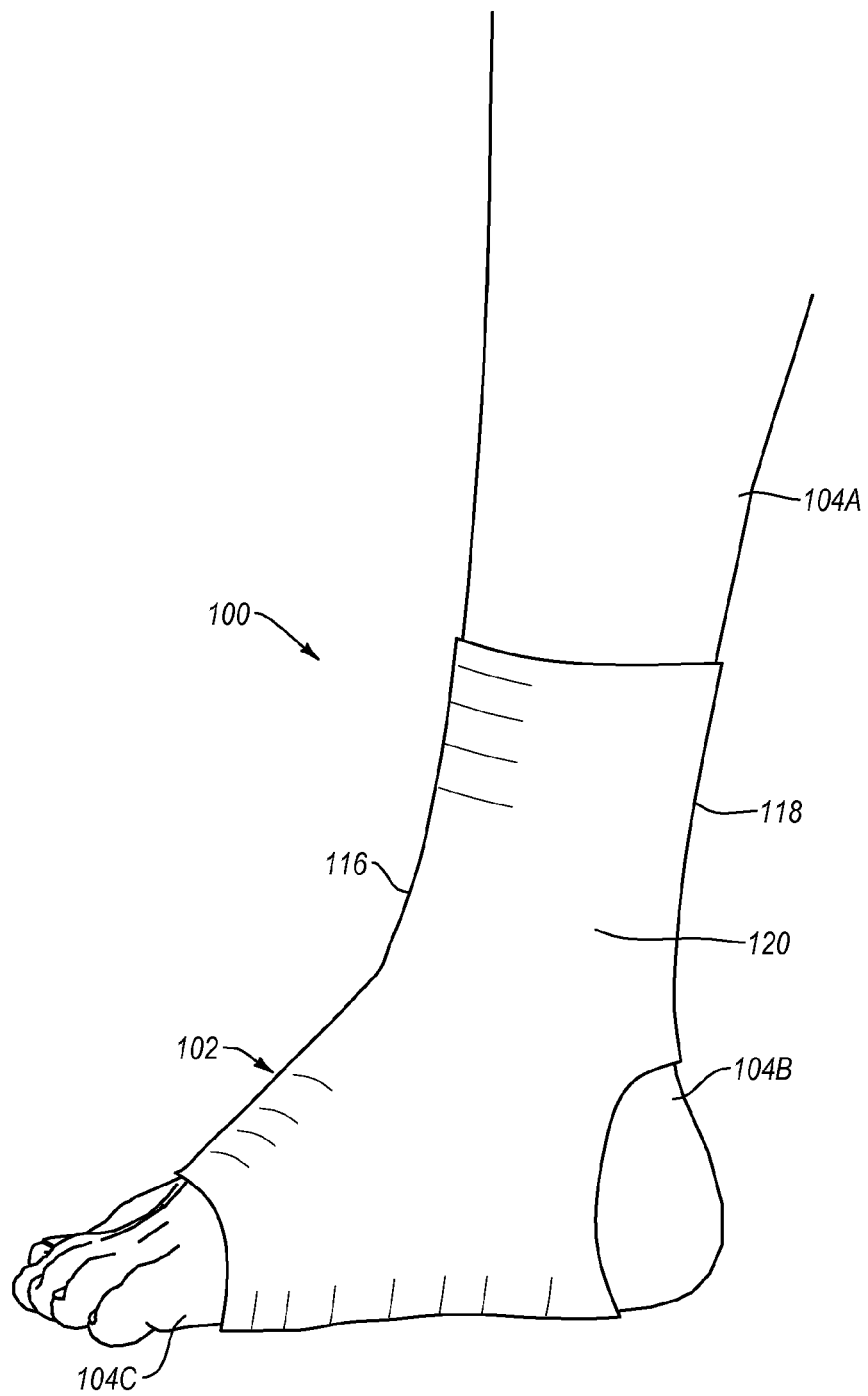

As shown in FIG. 2C, with the ankle brace 100 positioned on the user, the treatment 236 may be applied to at least the body 102 of the ankle brace 100 to move the ankle brace 100 from the receiving position to the supporting position (shown in FIG. 2D). In an embodiment, the treatment 236 may comprise a heat treatment. In other embodiments, the treatment 236 may comprise a chemical treatment, a water treatment, an electromagnetic radiation treatment, combinations thereof, or other suitable treatments.

Figure 2E:
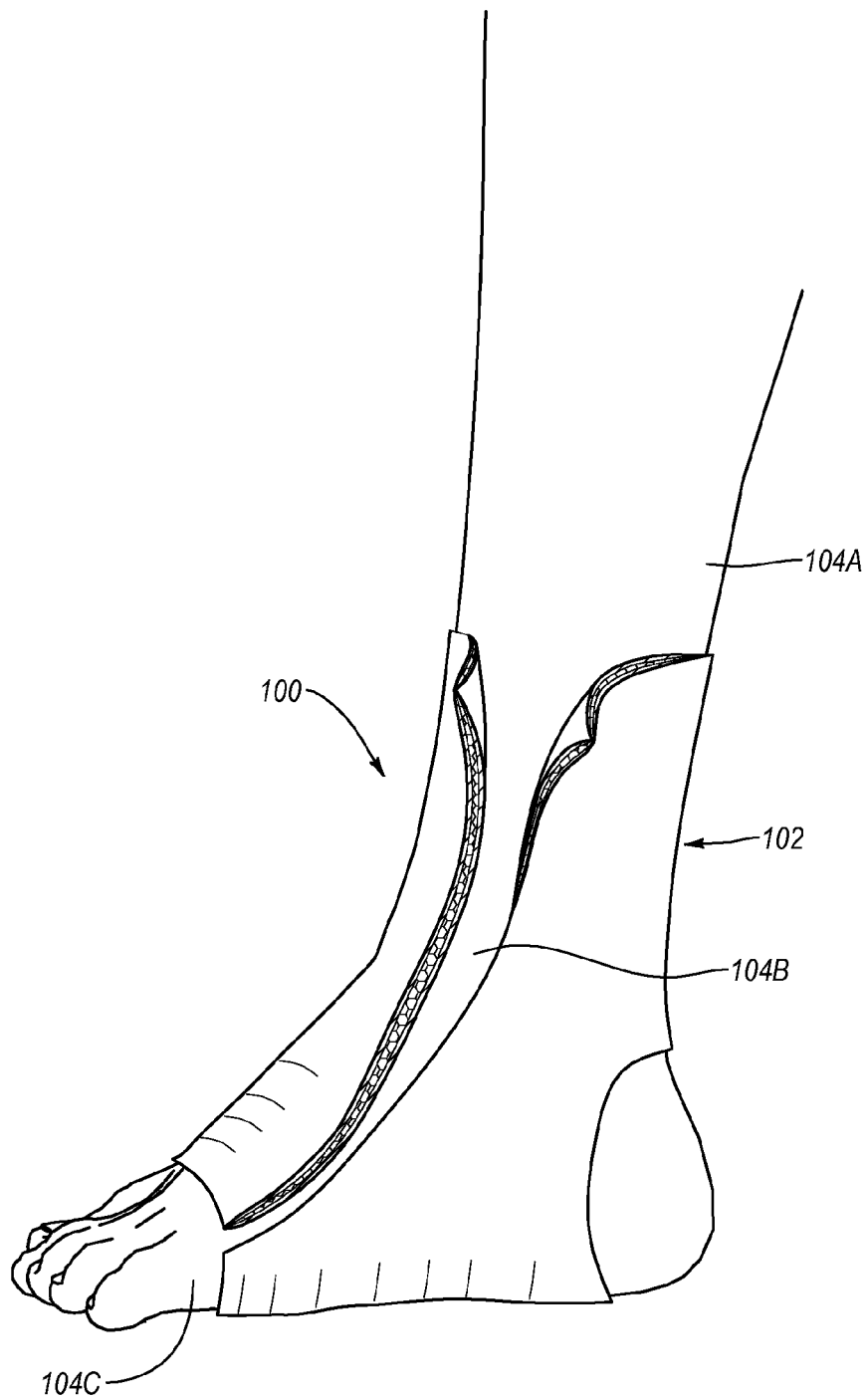

In the supporting position, the ankle brace 100 may shrink or reduce in size to conform to at least a portion of the foot 104C, ankle 104B, and/or leg 104A of the user as shown in FIG. 2D. The ankle brace 100 may shrink along a longitudinal axis of the ankle brace 100 and/or in a radial direction relative to the longitudinal axis. As described above, the ankle brace 100 in the supporting position may also be configured to at least partially restrict movement of the ankle 104B of the user in one or more directions. For example, the first side portion 120 and/or the second side portion 122 (not shown) of the ankle brace 100 may include a relatively stiff material and/or thickness T configured to restrict abnormal eversion and/or inversion of the ankle 104B and/or foot 104C. In addition, the front portion 116 and/or the back portion 118 may include a relatively flexible material and/or thickness T configured to allow dorsiflexion and/or plantar flexion of the ankle 104B. Accordingly, the ankle brace 100 may provide a user a customizable, quick-fit, orthopedic device. Once a user is finished with the ankle brace 100, the ankle brace 100 may be easily cut away to be removed as shown in FIG. 2E.

Figure 3A:
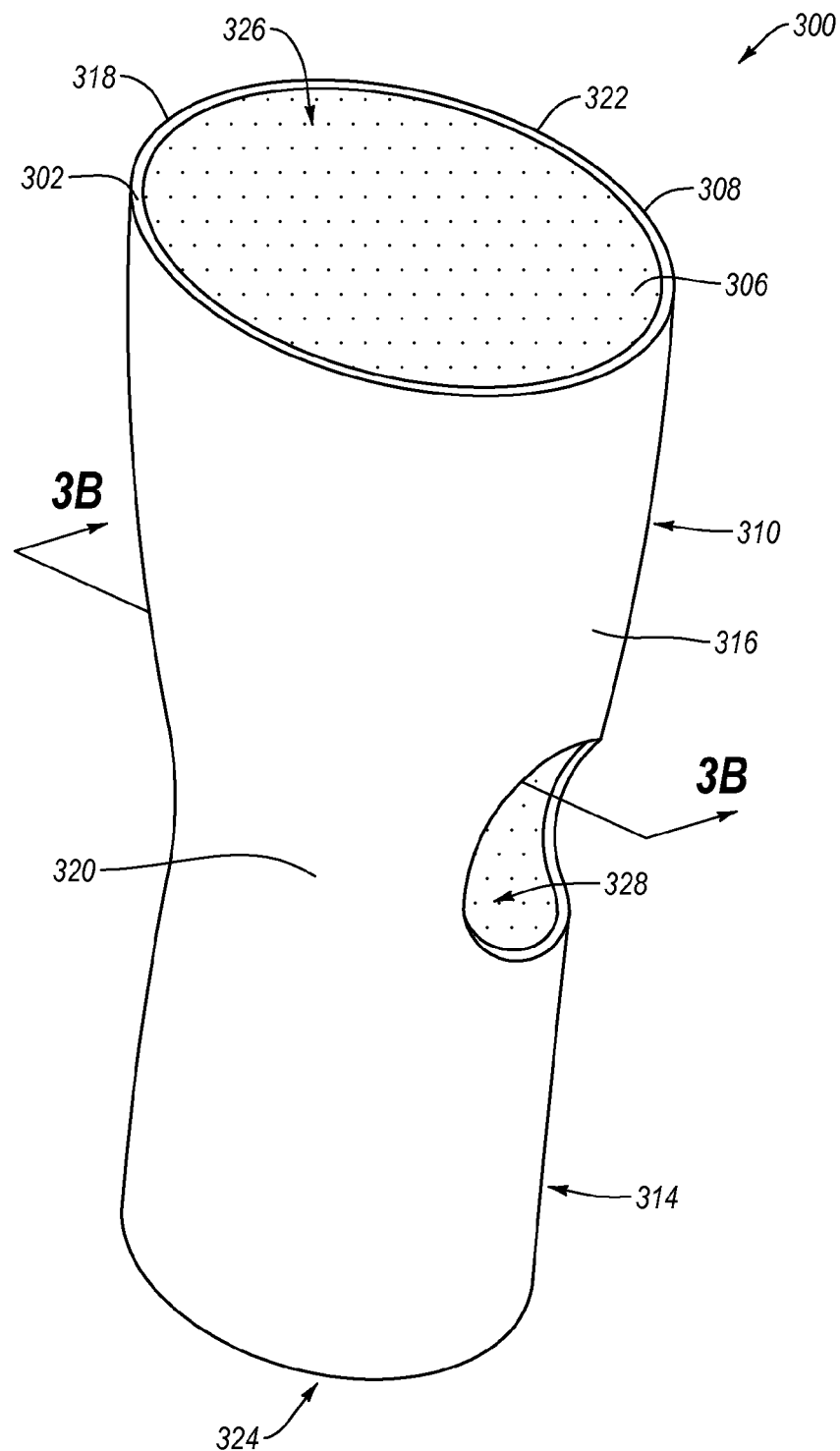
FIG. 3A illustrates a perspective view of a knee support according to an embodiment.
Figure 3B:
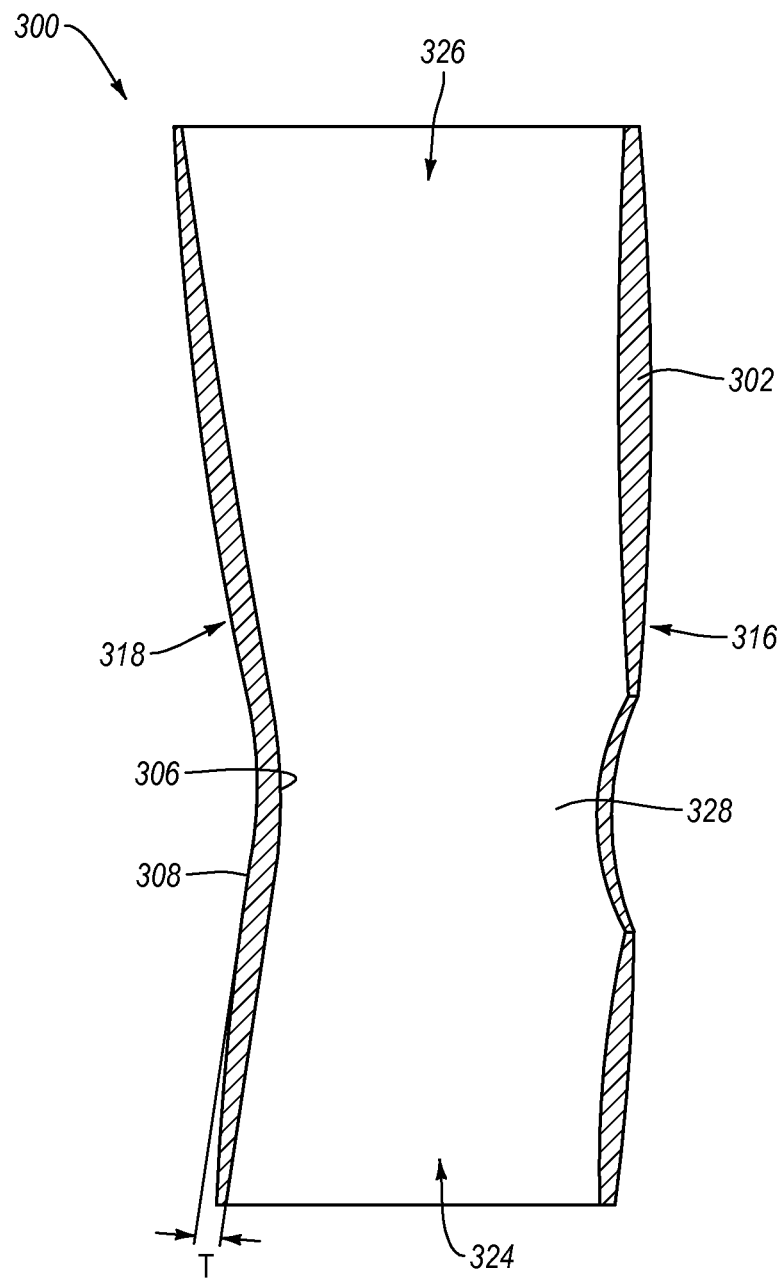
FIG. 3B illustrates a cross-sectional view of the knee support shown in FIG. 3A taken along line 3B-3B.

The concepts used in the ankle braces described above may also be employed in orthopedic devices comprising braces and supports including knee braces, neck braces, finger braces, wrist braces, shoulder supports, calf supports, back and lumbar supports, elbow supports, foot braces, chest braces, pelvic braces, and the like. For example, FIGS. 3A and 3B are perspective and cross-sectional views, respectively, illustrating a knee brace 300. The knee brace 300 may include a tubular body 302 forming an interior surface 306 and an exterior surface 308. As shown, the interior surface 306 may include features configured to help secure the knee brace 300 to a knee and/or leg of the user and/or provide a comfortable fit. For example, the interior surface 306 may include a plurality of small perforations for enhanced flexibility and/or ventilation of the knee brace 300. The body 302 may be at least partially defined by a front portion 316, a back portion 318, a first side portion 320, and a second side portion 322. The body 302 may also include a lower portion 314 and an upper portion 310. The upper portion 310 may be sized and configured to receive and/or generally surround at least a portion of the knee and a lower portion of a user's upper leg. As shown, the upper portion 316 may include a second opening 326 configured to allow a user to insert the user's leg through the knee brace 300. The lower portion 314 may be sized and configured to receive and/or generally surround at least a portion of the knee and an upper portion of a user's lower leg. As shown, the lower portion 314 may include a first opening 324 configured to allow the user's leg to pass through the body 302. The knee brace 300 may also include a third opening 328 configured to receive and/or position the patella of the user. In other embodiments, the third opening 328 may be omitted. One will appreciate that the knee brace 300 may be configured to be used on a user's right knee or left knee.

The knee brace 300 may include any of the shrinkable materials discussed above for the ankle brace 100 and may be configured to move between a receiving position, wherein the knee brace 300 may receive and/or loosely surround the knee, and a supporting position, wherein the knee brace 300 substantially conforms to and/or supports at least a portion of the knee. In the supporting position, the knee brace 300 may further be configured to immobilize, restrain, protect, and/or position the knee. In an embodiment, the knee brace 300 may move from the receiving position to the supporting position in response to a treatment 436 (shown in FIG. 4B) which may comprise a heat treatment, a chemical treatment, a water treatment, an electromagnetic radiation treatment, combinations thereof, or other suitable treatments.

FIG. 3B is a cross-section of the knee brace 300 taken along section line 3B-3B. As shown, the body 302 may have a thickness T extending between the interior surface 306 and the exterior surface 308 of the body 302. Depending on the application, the thickness T may be about 0.5-mm to 30-mm; 2-mm to 20-mm; or 3-mm to 10-mm. For example, the thickness T of the body 302 may be about 30-mm and may be configured to be more stiff to immobilize and/or position the knee in an emergency or treatment situation. In other embodiments, the thickness T may be either greater or smaller. For example, the thickness T of the body 302 may be relatively thin such that the knee brace 300 is generally lighter weight. Similar to the body 102, the thickness T of the body 302 may be generally uniform or may vary. For example, the thickness T of the body 302 may vary based on the anatomy. The body 302 may have a greater thickness T about the lateral and/or medial portions of the knee and a lesser thickness T about the posterior and/or anterior portions of the knee to position and/or support movement of the knee. In other embodiments, the thickness T of the body 302 may have a greater thickness T on the first side portion 320 and/or the second side portion 322 configured to apply pressure on the iliotibial band of a user. In addition, the thickness T of the body 302 may vary to influence stiffness and/or flexibility of the knee brace 300 in different locations and/or directions. For example, the first side portion 320 and/or the second side portion 322 of the body 302 may have a greater thickness T than other portions of the body 302 to give the knee brace 300 increased lateral and/or medial support and/or protection. In other embodiments, the knee brace 300 may include a liner and/or intermediate layer similar to those generally described in relation to ankle brace 100.

Figure 3C:
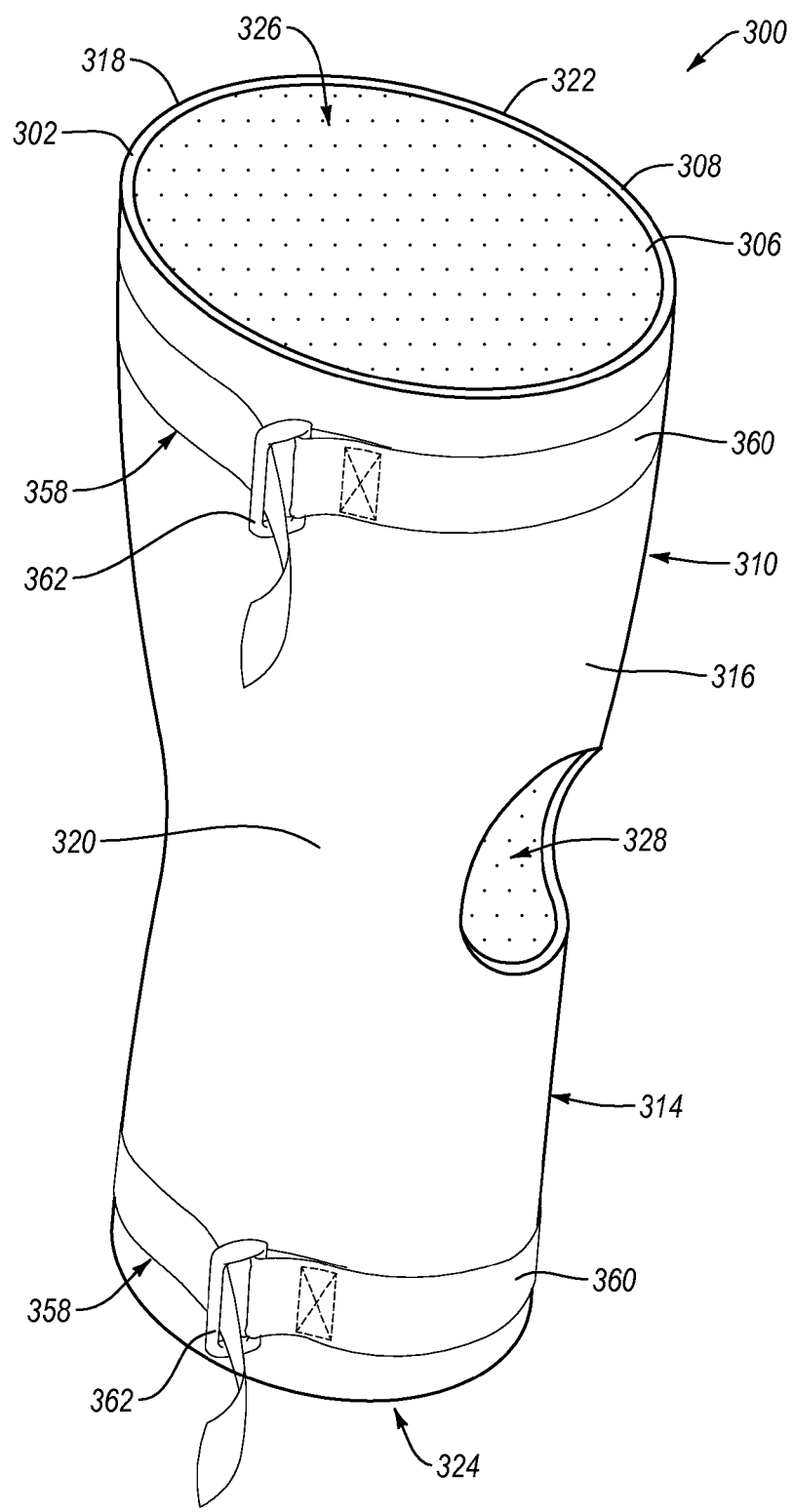
FIG. 3C illustrates a perspective view of a knee support according to another embodiment.

In other embodiments, the knee brace 300 may include one or more strap assemblies 358 tightenable by the user for further securing the knee brace 300 to the user's leg. In an embodiment, each of the one or more strap assemblies 358 may include a strap 360 having a first end, and second end, and a buckle 362 as shown in FIG. 3C. The first end of the strap 360 may pass through the buckle 362, doubled over itself, and may be fixed to itself. Accordingly, once the knee brace 300 is in the receiving position, a user may further secure the knee brace 300 to the user's leg with the one or more strap assemblies 358 as desired.

Figure 3D:
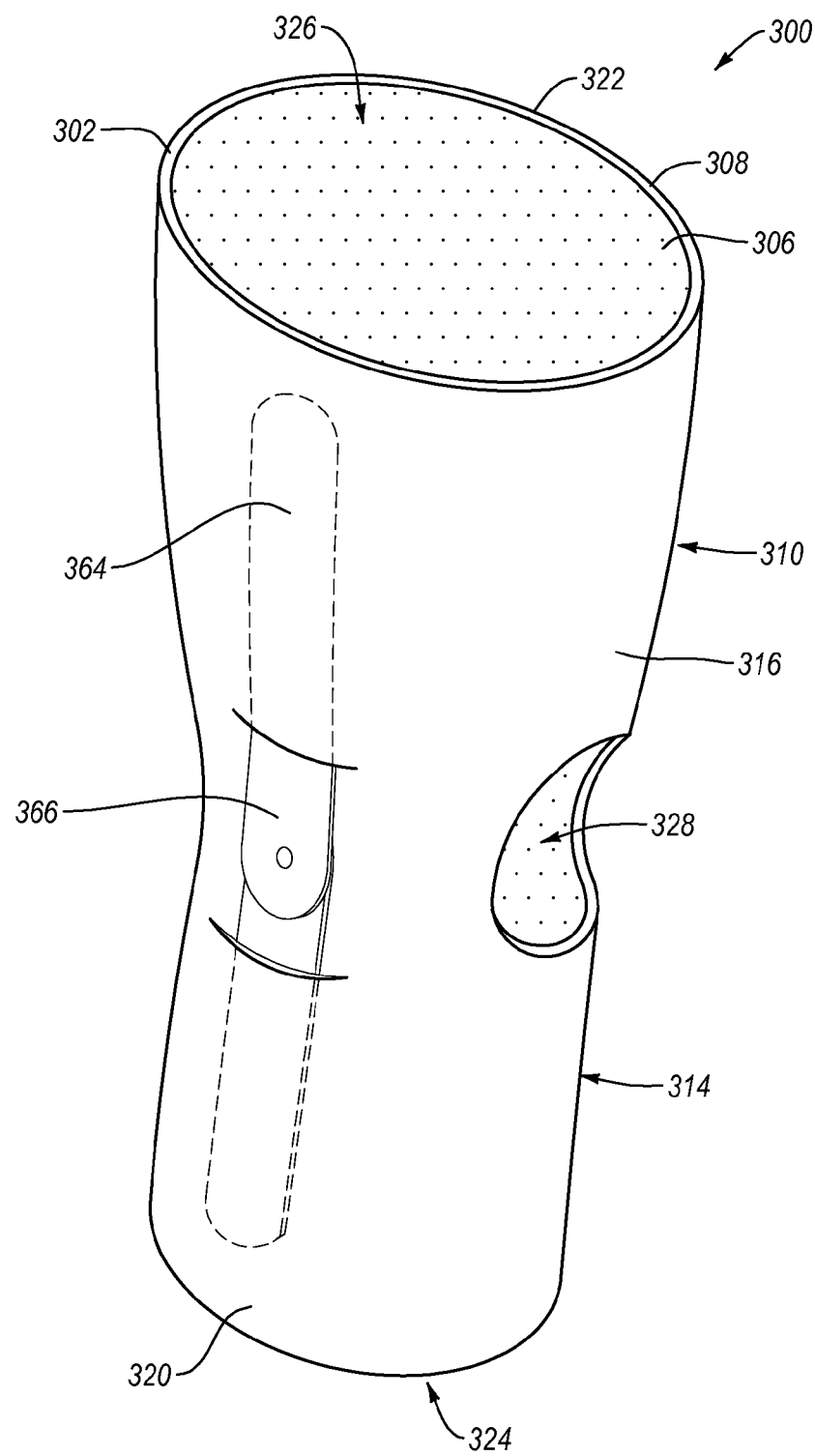
FIG. 3D illustrates a perspective view of a knee support according to another embodiment.

In other embodiments, the knee brace 300 may include one or more pockets 364 on the exterior surface 308 of the body 302 as shown in FIG. 3D. The one or more pockets 364 may be configured, for example, to receive one or more hinged support bars 366. Accordingly, once the knee brace 300 is in the receiving position, a user may insert the one or more hinged support bars 366 into the one or more pockets 364 for further lateral and/or medial support. In other embodiments, the one or more pockets 364 may be configured to receive other items including, but not limited to ice packs, heat packs, medical substances, magnets, sports gels, playbooks, keys, money, or the like.

Figure 4A:
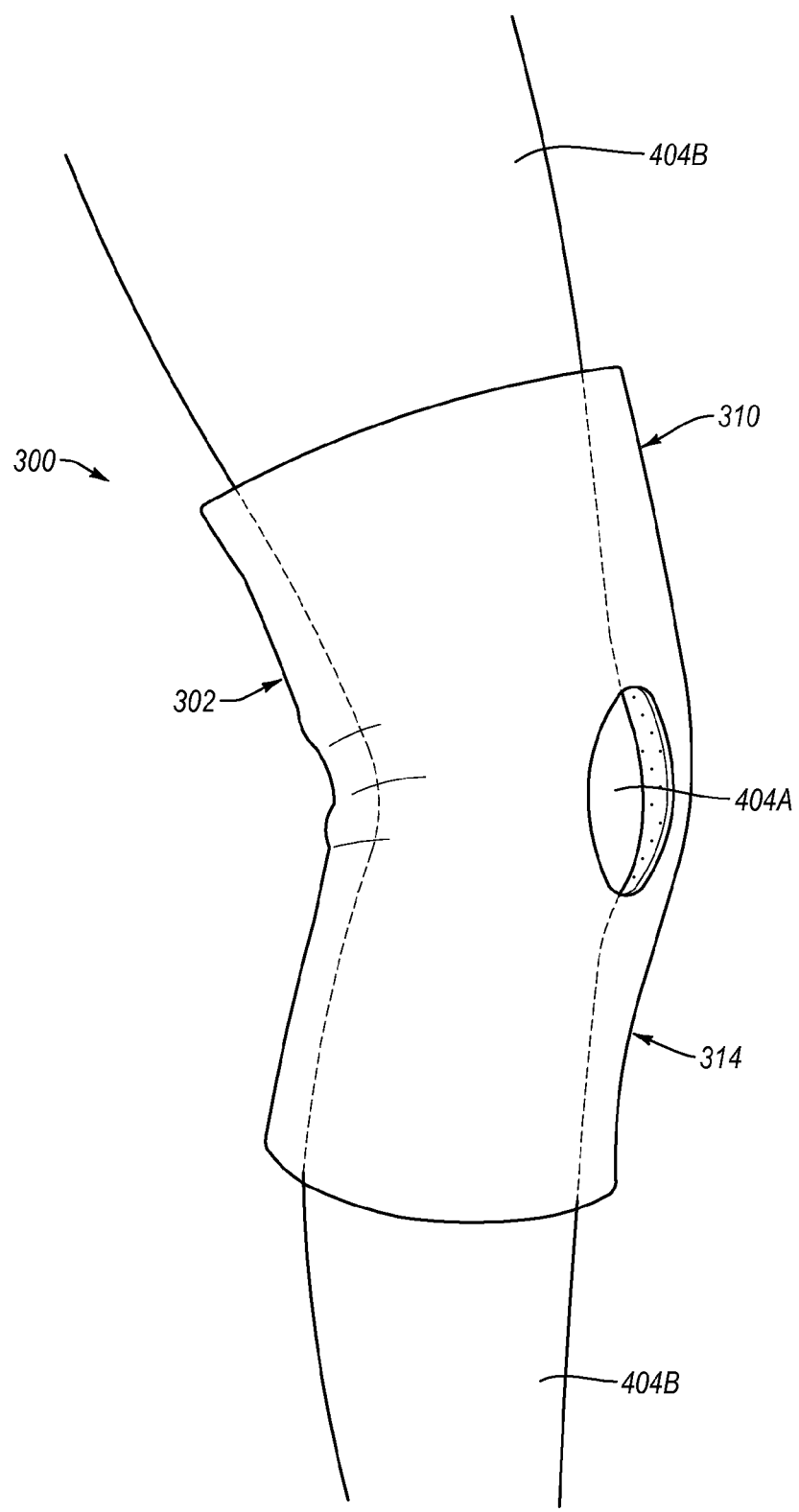
FIGS. 4A-4C illustrate perspective views illustrating exemplary steps in a method of using the knee support shown in FIG. 3A.

A method of using the knee brace 300 as shown in FIG. 3A will now be described in relation to FIGS. 4A-4C. As shown in FIG. 4A, with the knee brace 300 in the receiving position, a knee 404A and leg 404B may be positioned in the knee brace 300. In the receiving position, the upper portion 310 may loosely surround at least a portion of the knee 404A and a lower portion of the user's upper leg 404B. The lower portion 314 may loosely surround at least a portion of the knee 404A and an upper portion of the user's lower leg 404B. Such a configuration may allow the knee brace 300 to be easily and quickly positioned over the knee 404A of the user.

Figure 4B:
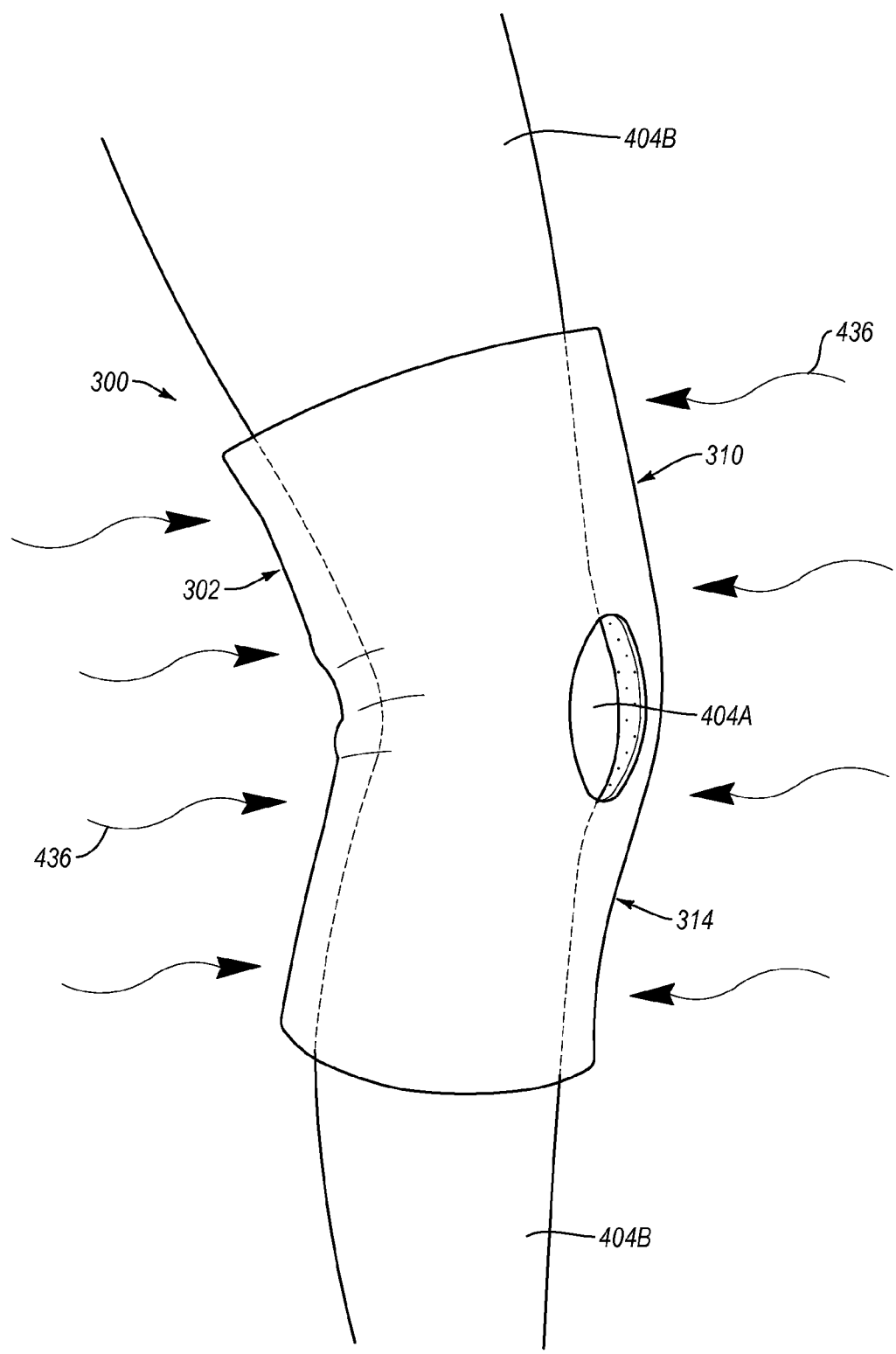
Figure 4C:
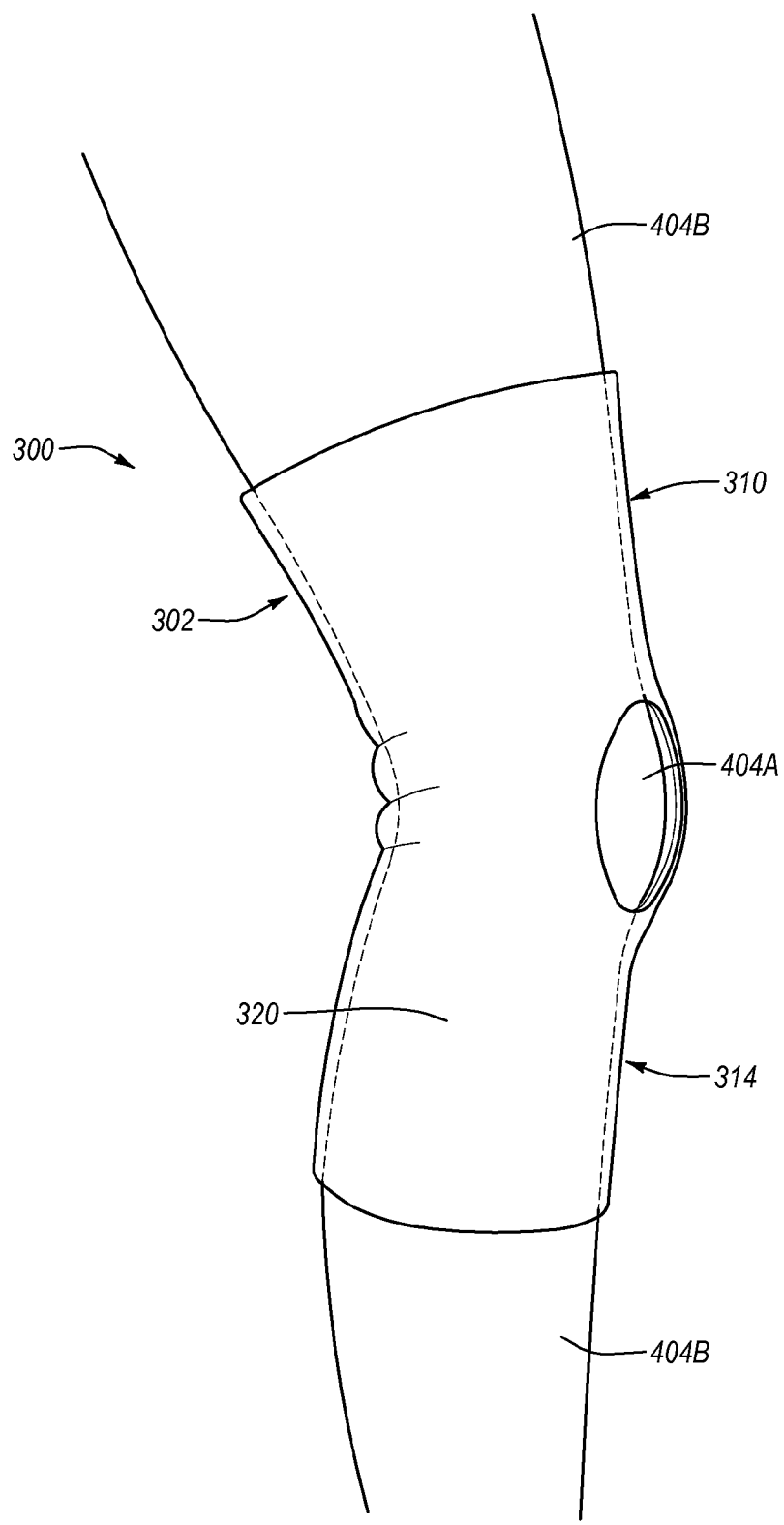

As shown in FIG. 4B, with the knee brace 300 positioned on the user's knee, the treatment 436 may be applied to at least the body 302 of the knee brace 300 to move the knee brace 300 from the receiving position to the supporting position (shown in FIG. 4C). In an embodiment, the treatment 436 may comprise a heat treatment, a chemical treatment, a water treatment, an electromagnetic radiation treatment, combinations thereof, or other suitable treatments.

In the supporting position, the knee brace 300 may shrink or reduce in size to conform to at least a portion of the knee 404A of the user shown in FIG. 4C. The knee brace 300 may shrink along a longitudinal axis of the knee brace 300 and/or in a radial direction relative to the longitudinal axis. As described above, the knee brace 300 in the supporting position may be configured to support at least a portion of the knee 404A and/or the patella of the user. For example, the first side portion 320 and/or the second side portion 322 of the knee brace 300 may include a relatively stiff material and/or a thickness T to provide medial and/or lateral support to the knee 404A of the user. Accordingly, the knee brace 300 may provide a user a customizable, quick-fit, orthopedic device.

Figure 5A:
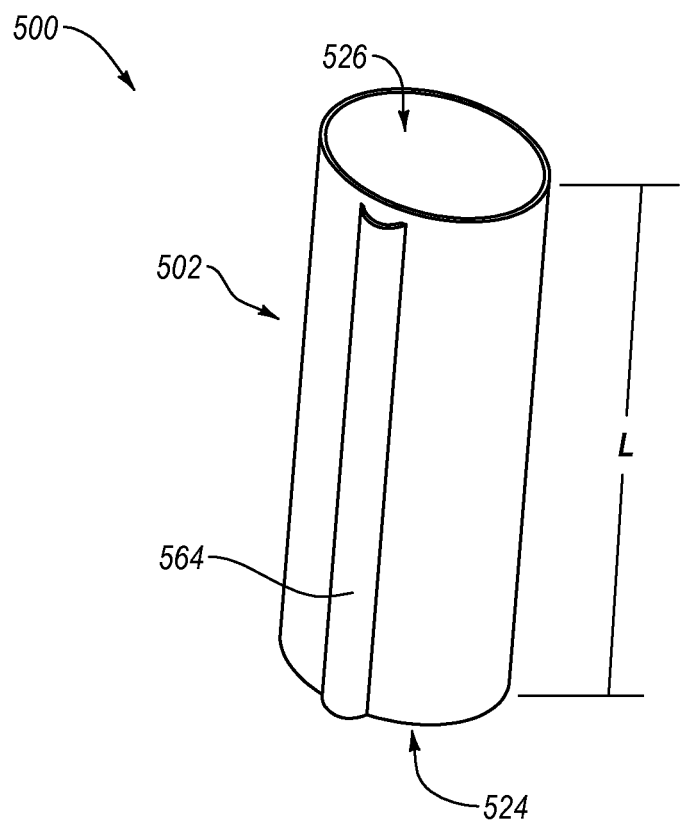
FIG. 5A illustrates a perspective view of a finger support according to an embodiment.
Figure 5B:
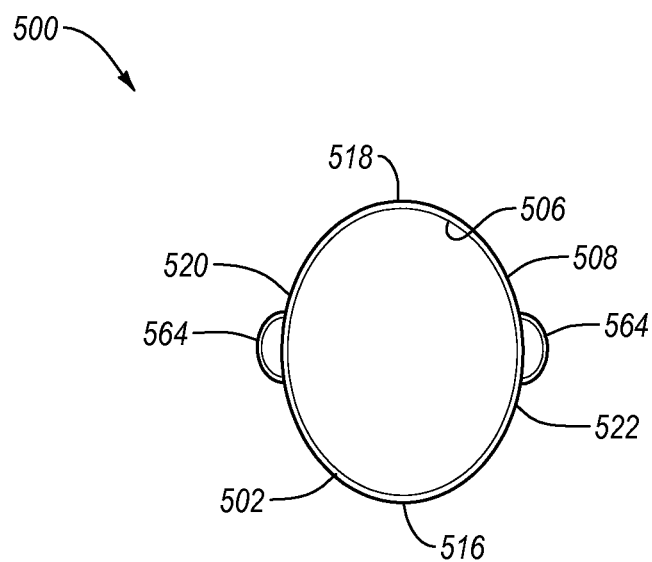
FIG. 5B illustrates a top plan view of the finger support shown in FIG. 5A.

FIGS. 5A and 5B are perspective and top plan views, respectively, illustrating a finger support 500 according to another embodiment. The finger support 500 may include a tubular body 502 forming an interior surface 506 and an exterior surface 508. The body 502 may be at least partially defined by a front portion 516, a back portion 518, a first side portion 520, and a second side portion 522. As illustrated, the body 502 may include a first opening 524 and a second opening 526 configured to allow a user to insert a user's finger through the finger support 500. The body 502 may also include a thickness (not shown) extending between the interior surface 506 and the exterior surface 508. The body 502 may also include a length L extending between the first opening 524 and the second opening 526 and one or more pockets 564 extending along at least a portion of the length L. The one or more pockets 564 may be configured to receive one or more stents, hinged support bars, magnets, ice packs, heat packs, medical substances, combinations thereof, or the like. In other embodiments, the one or more pockets 564 may be omitted.

The finger support 500 may include any of the shrinkable materials discussed above for the ankle brace 100 and/or the knee brace 300 and may be configured to move between a receiving position, wherein the finger support 500 may receive and/or loosely surround the finger, and a supporting position, wherein the finger support 500 substantially conforms to and/or at least partially restricts movement of at least a portion of the finger in one or more directions. In an embodiment, the finger support 500 may move from the receiving position to the supporting position in response to a treatment 636 (shown in FIG. 6B) which may comprise a heat treatment, a chemical treatment, a water treatment, an electromagnetic radiation treatment, combinations thereof, or other suitable treatments. The finger support 500 may be configured to be used with any of the user's fingers.

Figure 6A:
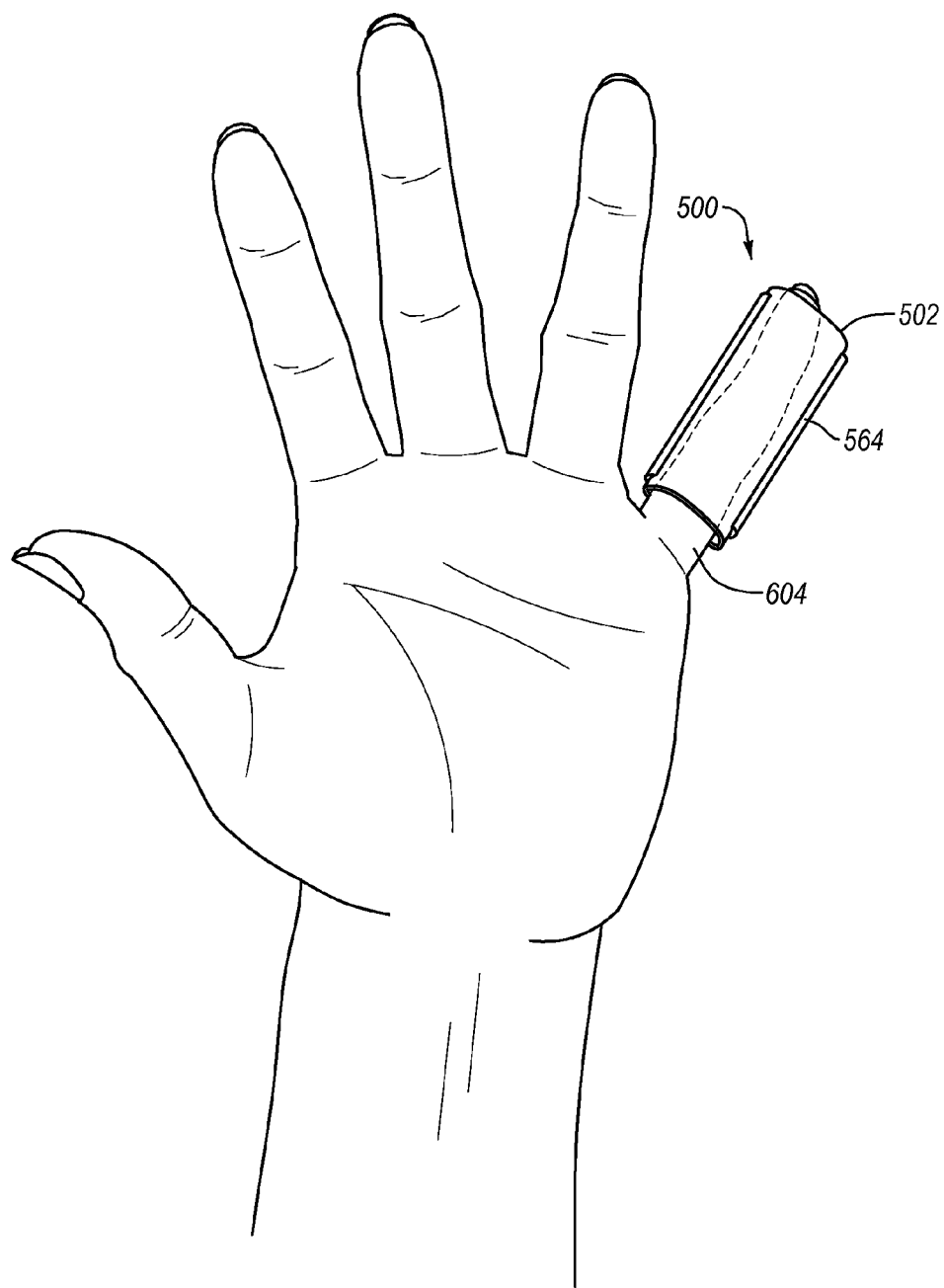
FIGS. 6A-6D illustrate perspective views illustrating exemplary steps in a method of using the finger support shown in FIG. 5A.

A method of using the finger support 500 will now be described in relation to FIGS. 6A-6D. As shown in FIG. 6A, with the finger support 500 in the receiving position, the finger support 500 may be positioned over the user's finger 604. In the receiving position, the body 502 may loosely surround at least a portion of the finger. Such a configuration may allow the finger support 500 to be easily and quickly positioned over the finger of the user.

Figure 6B:
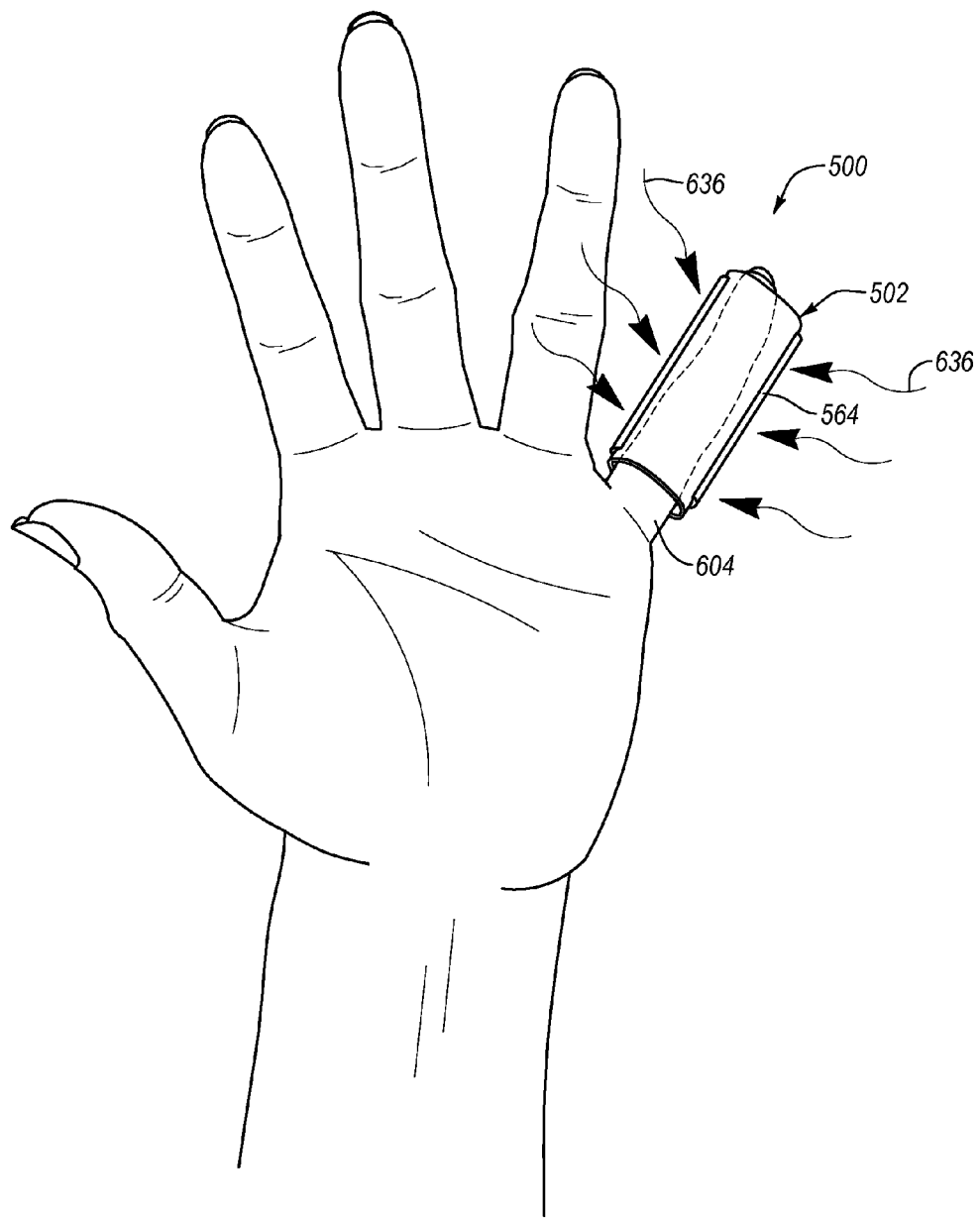
Figure 6C:
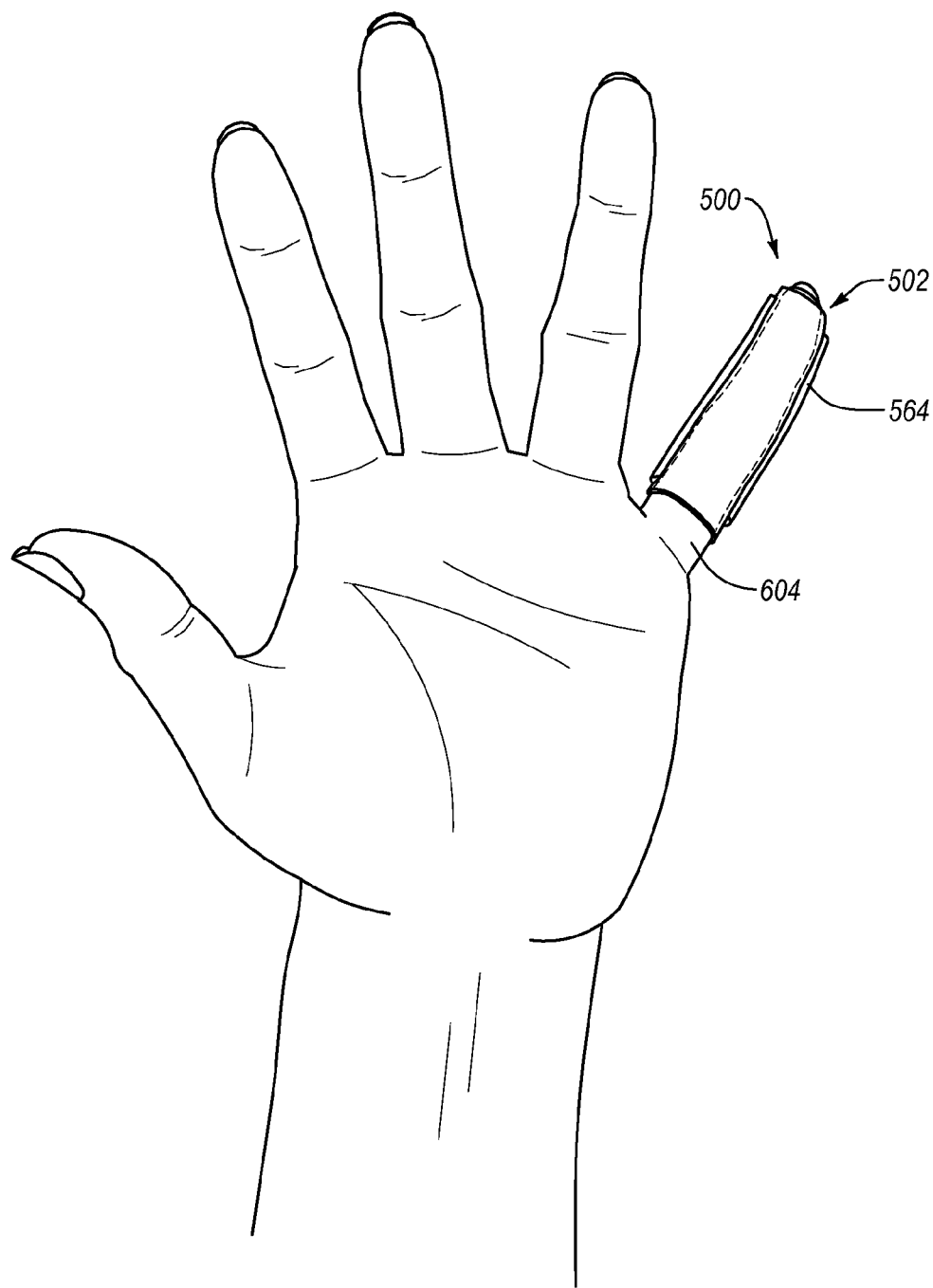
Figure 6D:
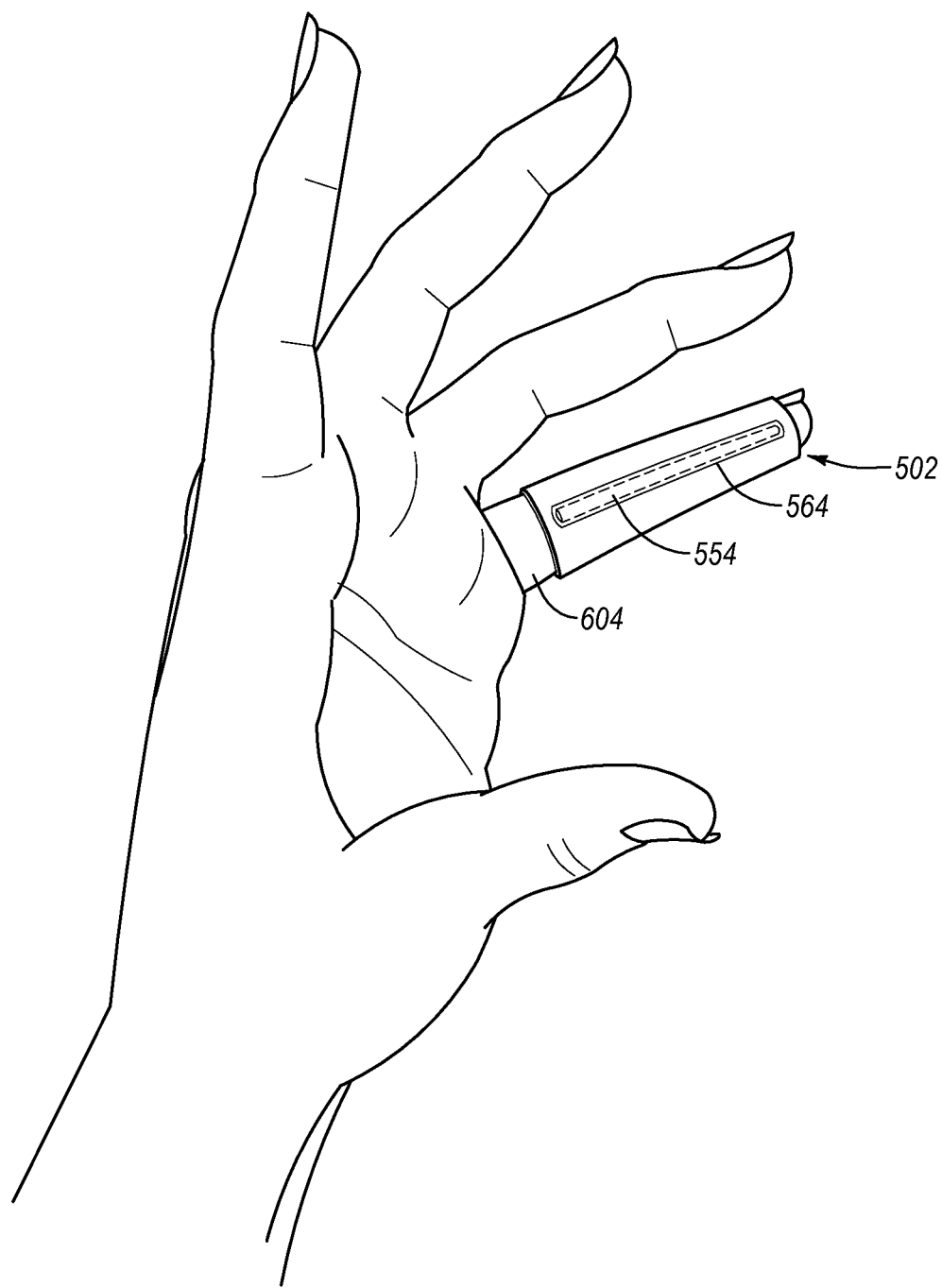

As shown in FIG. 6B, with the finger support 500 positioned on the user's finger, the treatment 636 may be applied to the finger support 500 to move the finger support 500 from the receiving position to the supporting position (shown in FIG. 6C). In the supporting position, the finger support 500 may shrink or reduce in size to conform to at least a portion of the finger 604 of the user as shown in FIG. 6C. The finger support 500 may shrink along the length L or a longitudinal axis of the finger support 500 and/or in a radial direction relative to the longitudinal axis. For example, the finger support 500 may shrink radially relative the longitudinal axis while maintaining substantially the same length L. As described above, the finger support 500 in the supporting position may be configured to support at least a portion of the finger 604. For example, the shrinkable materials of the body 502 may be configured to become substantially stiff once the finger support 500 is in the supporting position. In addition, the finger support 500 in the supporting position may be further configured to support at least a portion of the finger 604 by inserting one or more stints 554 into the one or more pockets 564 as shown in FIG. 6D. While one or more stints 554 are illustrated, in other embodiments, one or more hinged support bars, ice packs, heat packs, medical substances, or the like may be inserted to the one or more pockets 564.

Although the orthopedic devices and systems described above have been discussed in the context of ankle braces, knee braces, finger supports, and applications, in other embodiments, the orthopedic devices and systems disclosed herein are not limited to such use and may be used for many different applications, if desired, without limitation. Thus, such orthopedic devices and systems are not limited for use with ankle braces, knee braces, and finger supports and may be used with various other braces and supports, without limitation.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

What is claimed is:

1. An orthopedic device comprising:
   a tubular body forming an interior surface and an exterior surface and including:
      a leg portion including a first opening;
      a foot portion connected to said leg portion and including a second opening, said second opening positioned in a back portion of said foot portion and configured to receive a heel of the user;
      a thickness extending between said interior surface and said exterior surface, said thickness comprising a first thickness in side portions of said tubular body configured to provide lateral support to the ankle and a second thickness in a front portion of said tubular body, said first thickness being greater than said second thickness; and
      one or more shrinkable materials,
   said tubular body being moveable between a first position, wherein said tubular body is configured to at least partially receive and at least partially surround at least a portion of the ankle, and a second position, wherein one or more portions of at least one of said leg portion or said foot portion are configured to generally conform to and at least partially restrict movement of the at least a portion of the ankle, and wherein said tubular body is configured to move from said first position to said second position in response to a treatment.

2. The orthopedic device of claim 1, wherein a side portion of said foot portion is substantially stiff in said second position and a front portion of said foot portion is substantially flexible in said second position.

3. The orthopedic device of claim 1, wherein said tubular body is configured to restrict at least one of abnormal eversion or abnormal inversion of the ankle in said second position.

4. The orthopedic device of claim 1, wherein said tubular body is substantially stiff in said second position.

5. The orthopedic device of claim 1, wherein said one or more shrinkable materials comprise at least one of a polyolefin, nylon, neoprene, silicone rubber, or woven fabric.

6. The orthopedic device of claim 1, wherein the treatment comprises at least one of a chemical treatment or an ultraviolet light treatment.

7. The orthopedic device of claim 1, further comprising a liner positionable proximate said interior surface of said tubular body, said liner being configured to substantially protect at least one of the ankle or the foot from the treatment.

8. The orthopedic device of claim 1, further comprising a liner and an intermediate layer interposed between said liner and said interior surface of said tubular body, said intermediate layer being configured to substantially insulate at least one of the ankle or foot from the treatment, wherein the treatment comprises a heat treatment.

9. An orthopedic device intended for use with at least one moveable body part of a user, the orthopedic device comprising: a tubular body forming an interior surface and an exterior surface and including:
   at least one opening;
   a thickness extending between said interior surface and said exterior surface, said thickness comprising:
     a first thickness in side portions of said tubular body, said first thickness configured to provide lateral support to the at least one moveable body part; and
     a second thickness in a front portion of said tubular body, wherein said first thickness is greater than said second thickness; and
  one or more shrinkable materials, said tubular body being moveable between a first position, wherein said tubular body is configured to at least partially receive and at least partially surround the at least one moveable body part of the user, and a second position, wherein one or more portions of said tubular body are configured to generally conform to and at least partially restrict movement of the at least one moveable body part in one or more directions, and wherein said tubular body is configured to move from said first position to said second position in response to a treatment.

10. The orthopedic device of claim 9, wherein said tubular body includes a leg portion, a foot portion, and a second opening in a back portion of said foot portion configured to receive a heel of the user, and wherein the at least one moveable body part comprises at least a portion of an ankle.

11. The orthopedic device of claim 9, wherein said tubular body includes a second opening configured to allow a leg to pass through said tubular body and a third opening configured to position a patella, and wherein the at least one moveable body comprises at least a portion of a knee.

12. The orthopedic device of claim 9, wherein said tubular body is substantially stiff in said second position.

13. The orthopedic device of claim 9, wherein said one or more shrinkable materials comprises: a first shrinkable material in side portions of said tubular body, said first shrinkable material being configured to be substantially stiff in said second position; and a second shrinkable material in at least a front portion of said tubular body, said shrinkable material being configured to be substantially flexible in said second position.

14. The orthopedic device of claim 9, wherein the treatment comprises a heat treatment.

15. The orthopedic device of claim 9, wherein said one or more shrinkable materials comprise at least one of a polyolefin, nylon, neoprene, silicone rubber, or woven fabric.

16. An orthopedic device comprising:
   a tubular body forming an interior surface and an exterior surface and including:
     a first opening and a second opening configured to allow a leg to pass through said tubular body;
     a third opening configured to position a patella;
     a thickness extending between said interior surface and said exterior surface, said thickness comprising a first thickness in side portions of said tubular body configured to provide lateral support to the at least a portion of the knee and a second thickness in a front portion of said tubular body, said first thickness being greater than said second thickness; and
   one or more shrinkable materials,
  said tubular body being moveable between a first position, wherein said tubular body is configured to at least partially receive and at least partially surround at least a portion of a knee of the user, and a second position, wherein one or more portions of said tubular body are configured to generally conform to and at least partially restrict movement of the at least a portion of the knee in one or more directions, and wherein said tubular body is configured to move from said first position to said second position in response to a treatment.

17. The orthopedic device of claim 16, wherein said one or more shrinkable materials comprises: a first shrinkable material in side portions of said tubular body, said first shrinkable material being configured to be substantially stiff in said second position; and a second shrinkable material in at least a front portion of said tubular body, said shrinkable material being configured to be substantially flexible in said second position.

18. The orthopedic device of claim 16, wherein said tubular body shrinks in at least a radial direction relative to a longitudinal axis of said tubular body to move from said first position to said second position.

\* \* \* \* \*